US007011977B2

(12) United States Patent
Chace et al.

(10) Patent No.: US 7,011,977 B2
(45) Date of Patent: Mar. 14, 2006

(54) QUANTIFICATION OF CARNITINE LEVELS IN DIALYSIS PATIENTS

(75) Inventors: Donald H. Chace, Upper St. Clair, PA (US); GianFranco Fornasini, North Bethesda, MD (US)

(73) Assignee: Sigma-Tau Pharmaceuticals, Inc., Gaithersburg, MD (US)

(*) Notice: Subject to any disclaimer, the term of this patent is extended or adjusted under 35 U.S.C. 154(b) by 191 days.

(21) Appl. No.: 10/252,115

(22) Filed: Sep. 23, 2002

(65) Prior Publication Data
US 2003/0129762 A1  Jul. 10, 2003

Related U.S. Application Data

(63) Continuation-in-part of application No. 09/464,132, filed on Dec. 16, 1999, now Pat. No. 6,455,321, which is a continuation-in-part of application No. 09/277,119, filed on Mar. 26, 1999, now Pat. No. 6,258,605.

(60) Provisional application No. 60/117,880, filed on Jan. 30, 1999.

(51) Int. Cl.
*G01N 33/00* (2006.01)
(52) U.S. Cl. .......................... 436/86; 436/173
(58) Field of Classification Search .................. 436/86, 436/173
See application file for complete search history.

(56) References Cited

U.S. PATENT DOCUMENTS

| | | | | |
|---|---|---|---|---|
| 5,252,489 A | * | 10/1993 | Macri | 436/87 |
| 5,316,917 A | * | 5/1994 | Roe | 435/15 |
| 6,258,605 B1 | | 7/2001 | Chace | 436/86 |
| 6,335,369 B1 | * | 1/2002 | Cavazza | 514/561 |
| 6,429,230 B1 | * | 8/2002 | Cavazza | 514/561 |
| 6,455,321 B1 | * | 9/2002 | Chace | 436/173 |
| 6,653,349 B1 | * | 11/2003 | Cavazza | 514/547 |
| 6,696,492 B1 | * | 2/2004 | Cavazza et al. | 514/556 |
| 6,696,493 B1 | * | 2/2004 | Cavazza | 514/561 |

OTHER PUBLICATIONS

Savica et al. "Plasma & Muscle Carnitine Levels in Haemodialysis Patients with Morphological-Ulstructural Examination of Muscle Samples," Nephron 35: 232-236 (1983).*
Rodriguez-Segade et al. "Carnitine deficiency in haemodialysed patients," Clinical Chimica Acta, 159: 249-256 (1986).*

(Continued)

*Primary Examiner*—Moniquet T. Cole
(74) *Attorney, Agent, or Firm*—Hogan & Hartson L.L.P.

(57) ABSTRACT

Disclosed herein are methods for diagnosing carnitine deficiency in patients and quantifying that deficiency such that carnitine concentrations can be easily and accurately tracked within a given patient over time. Particular embodiments disclosed herein pertain to methods for diagnosing and quantifying the level of carnitine deficiency in patients undergoing dialysis procedures. The diagnosing and quantifying methods allow high throughput and low cost handling while providing high sensitivity and accuracy analysis such that the methods can be used frequently to monitor patient status, diagnose carnitine deficiency, and manage appropriate therapies to treat carnitine deficiency. The preferred embodiments disclosed herein utilize plasma samples taken from patients and dried on filter paper, which samples are then later analyzed using electrospray tandem mass-spectrometry and quantified in a manner that accounts for various complications that can skew free carnitine, acylcarnitine, or total carnitine concentrations.

46 Claims, 2 Drawing Sheets

OTHER PUBLICATIONS

Rodriguez-Segade et al. "Carnitine concentraions in dialysed and undialysed patients with chronic renal insufficiency," Ann. Clinical Biochemistry, 23: 671-675 (1986).*

Abdenur, J., et al.; Diagnosis of Isovaleric Acidaemia by Tandem Mass Spectrometry: False Positive Result due to Pivaloylcarnitine in a Newborn Screening Programme; J Inher Metab Dis 1998 21:624-630.

Abdenur, J., et al. MCAD Deficiency: Acylcarnitines (AC) by Tandem Mass Spectrometry (MS-MS) are Useful to Monitor Dietary treatment. Adv Exp Med Biol 1999; 466: 353-363.

Albers, S, et al. Detection of Neonatal Carnitine Palmitoyltransferase II Deficiency by Expanded Newborn Screening with Tandem Mass Spectrometry, Pediatrics 2001; 107:E103.

Barnes R., et al; Carnitine in Dried Blood Spots: A Method Suitable for Neonatal Screening. Clin Chim Acta 1991; 197:27-33.

Chace, D., et al; Electrospray Tandem Mass Spectrometry for Analysis of Acylcarnitines in Dried Postmortem Blood Specimens Collected at Autopsy from Infants with Unexplained Cause of Death. Clin Chem 2001; 47:1166-1182.

Chace, D., et al; Errors Caused by the Use of D,L-octanolycarnitine for Blood-Spot Calibrators. Clin Chem 2001; 47:758-760.

Clayton P., et al. Screening for Medium Chain Acyl-coA Dehydrogenase Deficiency using Electrospray Ionisation Tandem Mass Spectrometry. Arch Dis Child 1998; 79:109-115.

Gaskell, S., et al Differentation of Isomeric Acylcarnitines using Tandem Mass Spectrometry, Anal Chem 1986; 58: 2801-2805.

Gempel, K., et al. Adult Carnitine Palmitoyltransferase II Deficiency: Detection of Characteristic Carnitine Esters in Serum by Tandem Mass Spectrometry. J Inherit Metab Dis 1999; 22:941-942.

Johnson A., et al. The Use of Automated Electrospray Ionization Tandem MS for the Diagnosis of Inborn Errors of Metabolism from Dried Blood Spots. Biochem Soc Trans 1996; 24:932-938.

Johnson, D. Inaccurate Measurement of Free Carnitine by the Electrospray Tandem Mass Spectrometry Screening Methods for Blood Spots. J Inher Metab Dis 1999; 22:201-202.

Kodo, N., et al. Quantitative Assay of Free and Total Carnitine Using Tandem Mass Spectrometry, Clin. Cim Acta 1989; 186:383-390.

Liberato, D., et al. Analysis of Acylcarnitines in Human Metabolic Disease by Thermospray Liquid Chromatography/Mass Spectrometry , In: Burlingame A. A. Castagnoli N, editors. Mass Spectrometry in the Health and Life Sciences. Amsterdam, Netherlands: Elsevier Science Publishers, 1985; 333-348.

Millington D., et al. Application of Fast Atom Bombardment with Tandem Mass Spectrometry and Liquid Chromatogaphy/Mass Spectrometry to the Analysis of Acylcarnitines in Human Urine, Blood and tissue. Anal. Biochem. 1989; 180:331-339.

Millington, D., et al. Tandem Mass Spectrometry: A New Method for Acylcarnitines Profiling with Potential for Neonatal Screening for Inborn Errors of Metabolism. J Inher Metab Dis 1990; 13:321-324.

Millington, D., et al. The Analysis of Diagnostic Markers of Genetic Disorders in Human Blood and Urine using Tandem Mass Spectrometry with Liquid Secondary Ion Mass Spectrometry. Int'l Mass Spectrometry Ion Process 1991; 111:211-228.

Naylor, E. et al. Automated Tandem Mass Spectrometry for Mass Newborn Screening for Disorders in Fatty Acid, Organic Acid and Amino Metabolism. J Child Neurol 1999; 14:S4-S8.

Rashed, M., et al. Diagnosis of Inborn Errors of Metabolism from Blood Spots by Acylcarnitines and Amino Acids Profiling Using Automated Electrospray Tandem Mass Spectrometry. Pediatr Res 1995: 38:324-331.

Stevens R., et l. Assay for Free and Total Carnitine in Human Plasma Using Tandem Mass Spectrometry. Clin Chem 2000; 46:727-729.

Vreken, P., et al. Quantitative Plasma Acylcarnitine Analysis Using Electrospray Tandem Mass Spectrometry for the Diagnosis of Organic Acidaemias and Fatty Acid Oxidation Defects. J Inher Metab Dis 1999 22:302-306.

Wiley, V., et al Newborn Screening with Tandem Mass Spectrometry; 12 Months' Experience in NSW Australia. Acta Paediatr Suppl 1999; 88:48-51.

Yergey, A., et al. Thermospray Liquid Chromatrography/ Mass Spectrometry for the Analysis of L-Carnitine and its Short-Chain Acyl Derivates. Anal Biochem 1984; 139:278-283.

* cited by examiner

QUANTIFICATION OF CARNITINE LEVELS IN DIALYSIS PATIENTS

REFERENCE TO RELATED APPLICATIONS

This is a continuation-in-part of application Ser. No. 09/464,132, filed Dec. 16, 1999, now U.S. Pat. No. 6,455,321 issued Sep. 24, 2002, which application is a continuation-in-part of application Ser. No. 09/277,119, filed Mar. 26, 1999, now U.S. Pat. No. 6,258,605 issued Jul. 10, 2001, which in turn claims priority from provisional application Ser. No. 60/117,880, filed Jan. 30, 1999, the disclosures of all applications being entirely herein incorporated by reference.

FIELD OF THE INVENTION

The present invention relates to methods for quantifying the level of carnitine deficiency in patients such that carnitine concentrations can be easily and accurately tracked within a given patient over time. In particular, the present invention pertains to methods for quantifying the carnitine concentrations and the level of carnitine deficiency in patients undergoing dialysis procedures.

BACKGROUND OF THE INVENTION

Carnitine is a naturally occurring substance in the human body required for energy metabolism at the cellular level. It has been shown to have a role in transporting fatty acids into mitochondria to help produce energy and in removing toxic waste from the cells. Studies indicate that more than 70% of the carnitine present in the plasma of a hemodialysis patient is removed during a single dialysis session. This high percentage carnitine loss by a patient during a hemodialysis session is thought to be attributable to the compound's relatively small molecular weight, high water solubility, and poor protein binding. It is believed that carnitine levels are further diminished in end stage renal disease ("ESRD") patients by reduced renal synthesis and reduced intake of meat and dairy foods. Thus, the carnitine levels of dialysis patients, and end stage renal disease patients undergoing dialysis in particular, generally decrease steadily over time.

The depletion of carnitine levels in tissue is a noted long-term consequence of repeated losses of carnitine from plasma. Thus, carnitine depletion in tissue is experienced by patients that undergo successive dialysis sessions over a prolonged period of time. Tissue carnitine depletion is undesirable because it is associated as a possible causal factor for many health complications associated with dialysis, including cardiomyopathy, arrhythmias, muscle weakness, and general fatigue.

As described in U.S. Pat. Nos. 6,335,369 and 6,429,230 to Cavazza (henceforth, "the Cavazza patents"), the administration of levocarnitine (or L-carnitine) may be beneficially used to treat carnitine deficiency in ESRD patients (also known as "chronic uremic patients") undergoing regular dialysis. According to the Cavazza patents, ESRD patients undergoing periodical dialysis can be administered levocarnitine or one of its salts to prevent or treat carnitine deficiency. This is taught to be accomplished by, among other things, administering an effective dose of L-carnitine intravenously via a venous return line after each dialysis session of the ESRD patient. The Cavazza patents teach that initiation of such L-carnitine injection therapy to treat carnitine deficiency may be prompted by patients demonstrating pre-dialysis plasma carnitine concentrations that are below normal (normal carnitine concentration levels are 40–50 $\mu$mol/L). Such intravenous administration of L-carnitine to ESRD patients undergoing dialysis treatments is taught to result in increased plasma carnitine concentrations. Additionally, carnitine deficiency in ESRD patients who are undergoing dialysis can be prevented by the intravenous administration of levocarnitine prompted by carnitine concentration levels in plasma that are trending toward carnitine deficiency. The methods for the prevention of treatment of carnitine deficiency as taught by the Cavazza patents thereby make it possible to correct for the loss of plasma carnitine which otherwise could take place during a dialysis session.

In order to manage the therapeutic delivery of L-carnitine to dialysis patients, it would be beneficial for physicians to have an accurate and reliable, yet fast and low cost, method to monitor the level of plasma carnitine in patients before a given dialysis session, after a given dialysis session, and/or during a given dialysis session. The current techniques available for measuring carnitine levels in a patient's plasma include enzymatic assays, high-pressure liquid chromatography ("HPLC"), and tandem mass spectrometry ("MS/MS"). These techniques for quantifying plasma carnitine levels, however, do not generally provide the high throughput, low cost, and high sensitivity and accuracy analysis necessary for implementation on a large-scale basis to manage levocarnitine replacement therapies for patients undergoing dialysis.

Each of the contemporary techniques for measuring carnitine levels in patients suffers from distinct disadvantages. Enzymatic assays are highly sensitive, but are extremely time consuming to run and, therefore, are not readily adaptable to large-scale use by dialysis clinics. Furthermore, enzymatic assays can only provide quantification of free carnitine (L-carnitine) and total carnitine levels in a plasma sample and do not provide results for individual acylcarnitines, such as long chain carnitines, which are useful markers of the metabolic status of ESRD patients undergoing dialysis for selecting appropriate therapies. Furthermore, the determination of total carnitine levels using enzymatic assays must be carried out separately from the determination of free carnitine levels due to the necessary use of chemical hydrolysis prior to quantification.

HPLC methods involving specific pre-column derivatization and fluorescence detection have been demonstrated to be sufficiently sensitive to allow the determination of levels for several individual acylcarnitines. However, HPLC methods remain expensive and very time consuming, in large part because the sample preparation require elaborate, multi-step procedures. Furthermore, the determination of long chain and very long chain acylcarnitine levels cannot be carried out by HPLC. HPLC further suffers from the fact that the quantification of total carnitine levels requires a separate analytical run including chemical hydrolysis of the sample.

Notably, both the HPLC and enzymatic assays methods that can be used for accurate and reliable determination of carnitine levels require biological samples that have been kept frozen during storage and shipment following collection. Understandably, this factor makes remote laboratory utilization of these procedures difficult.

With regard to MS/MS quantification of carnitine levels, electrospray ionization MS/MS has been used to identify abnormal carnitine profiles in infants from blood samples. In particular, U.S. Pat. No. 6,258,605 to Chace ("the '605 patent") discloses a method for genetic screening of infants using tandem mass spectrometry ("MS/MS"). According to the '605 patent, blood is taken from an infant patient and spotted in small amounts on a piece of filter paper where it is dried and sent to a lab. The blood is then reconstituted at the lab and run through an electrospray ionization mass spectrometer with an internal standard to identify potentially abnormal metabolic profiles of amino acids and acylcarnitines. By collecting dried blood samples on filter paper, the method taught by the '605 patent allows for inexpensive, un-refrigerated transfer of blood samples from the doctor to a remote lab for analysis. This in turn permits a single, remotely located mass spectrometer to be used to handle a large volume of samples, thereby taking advantage of economies of scale.

Although electrospray ionization MS/MS of dried blood samples as taught by the '605 patent is a reliable, low cost and high throughput mechanism for identifying abnormal metabolic profiles of acylcarnitines in infants, it is not a suitable solution for obtaining accurate quantifications of plasma carnitine levels in carnitine deficient patients for several reasons. First, blood can be a poor indicator of tissue carnitine levels because the intracellular concentration of L-carnitine in red blood cells does not equilibrate with the plasma concentration (the membranes of the erythrocytes being impermeable to L-carnitine). Only the carnitine present in a patient's plasma can be dialyzed during a given dialysis session while the carnitine concentration within the red blood cells is not directly affected by dialysis. Furthermore, since red blood cells do not have mitochondria, carnitine cannot be utilized therein for the β-oxidation of long-chain fatty acids. Therefore, the intracellular concentration of carnitine present in red blood cells may in fact skew any analyses for carnitine deficiency. Preparation of dried blood samples for introduction into the mass spectrometer as taught in the '605 patent would necessarily release a large portion of carnitine from the red blood cells and thereby overstate the determination of free and total carnitine levels.

In addition, the derivation steps employed during sample preparation for many MS/MS analysis methods are known to cause hydrolysis of acylcarnitines into free carnitine, as has been reported by Johnson et al. (1999) among others. This hydrolysis of acylcarnitines can cause over-reporting of free carnitine. Unfortunately, such over-reporting of free carnitine is clinically significant if the method were to be used to manage carnitine replacement therapy for dialysis patients. Prior solutions to this problem entail running an MS/MS assay twice on a given sample, once without derivatization to measure free carnitine levels and a second time with derivatization to measure total carnitine levels. This, however, increases sample analysis costs and therefore loses a significant benefit of MS/MS methods. Furthermore, while MS/MS can be employed without a derivatization step, removal of this step causes the sensitivity of the assay to decrease over ten fold. This marked decrease in sensitivity is problematic in the quantification of carnitine deficiency because the screened samples taken from carnitine deficient patients undergoing dialysis are necessarily expected to have low levels of carnitine present.

A further complication to the adaptation of MS/MS to quantifying carnitine levels is that glutamic acid is believed to interfere with the analysis of acetylcarnitine concentrations. Tandem mass spectrometry is capable of distinguishing molecular ions of the same mass that also have different product ions. Tandem mass spectrometry, however, cannot distinguish between molecular masses having the same product ions and molecular ions. The di-butyl ester of the protonated from of glutamic acid shares the same molecular ion molecular mass (260 m/z) and product ion molecular mass (85 m/z) as the butyl ester of acetylcarnitine. Since glutamic acid in physiological concentrations is much more abundant than acetylcarnitine, the protonated form glutamic acid can be present in sufficient amounts that can interfere with the MS/MS signal at 260 m/z which is associated with the detection of acetylcarnitine. Therefore any utilization of MS/MS for analysis of carnitine concentrations must account for this problem.

Therefore, there remains a need in the art for an improved method for diagnosing carnitine deficiency in patients and quantifying the level of carnitine deficiency such that carnitine concentrations can be easily and accurately tracked within a given patient over time. Also, there remains a need in the art for a high throughput, low cost, and high accuracy method for quantifying the level of carnitine deficiency in a patient such that the method can be used frequently to monitor the level of carnitine deficiency and manage appropriate therapies to treat carnitine deficiency.

SUMMARY OF THE INVENTION

In light of the above-described deficiencies present in contemporary techniques for diagnosing and quantifying carnitine deficiency in patients undergoing dialysis, it is an object of the present invention to provide a reliable and accurate method for quantifying carnitine levels in dialysis patients.

Furthermore, it is an object of the present invention to provide a method for a high throughput, low cost, and high accuracy quantification of the level of carnitine deficiency in patients to help manage therapies for treating dialysis patients.

Additionally, it is an object of the present invention to provide a highly sensitive method for determining free carnitine, acylcarnitine and total carnitine levels in dialysis patients. Such levels can be utilized to track patient health and assist in diagnosing carnitine deficiency and in triggering preventative and/or treatment therapies.

The above-identified and other objects are achieved by the methods of the present invention as disclosed herein which include the quantitative analysis of free L-carnitine, acylcarnitines, and total carnitine in plasma specimens dried on filter paper through suitable methods including enzymatic assays, HPLC, and electrospray MS/MS. Methods of the present invention include specimen collection, preparation and analysis through quantitative calculations and comparisons of the samples with calibration and quality control samples prepared from dialyzed plasma.

Plasma samples are collected from a dialysis patient before, during and/or after each dialysis session and spotted on filter paper and dried. The dried samples are then sent (such as via overnight mail) to a remote laboratory location for analysis. The dried specimens are then prepared for analysis at the laboratory by reconstitution with an internal standard containing alcohol and then, preferably, derivatization. Prepared samples are analyzed to quantify free carnitine and acylcarnitine and their internal standards in the patient samples, calibration curve samples and quality control samples. The results of the quantification assays of the various samples are then computed to quantify free carnitine, acylcarnitine and total carnitines in the dried patient samples while accounting for, among other things, various sample collection and preparation complications, hydrolysis of acylcarnitines, interference by glutamate, and equipment performance.

Preferred embodiments of the invention analyze the samples by flow injection electrospray MS/MS using a variety of SRM and precursor ion scans. Preferably, methanol solutions which contain deuterized internal carnitine standards are used to extract the dried plasma samples from the filter paper, whether the plasma is from patient samples or known calibration curve samples or quality control samples. In most preferred embodiments, the extracted plasma samples are then followed up with gas drying and then esterification with acidified butanol, and any accompanying hydrolysis of acylcarnitines into free carnitine is accounted for in the MS/MS output data using appropriate calculations as disclosed herein.

Additional features and advantages of the invention will be set forth in the description that follows, and in part will be apparent from the description, or may be learned by practice of the invention. The invention will now be described in further detail with respect to particular embodiments thereof with reference to the figures depicted in the appended drawings. The above and other objectives and advantages of the invention will be realized and attained by the embodiments particularly pointed out in the written description and claims hereof as well as the appended drawings. The following detailed description and figures are intended to be illustrative of particular applications of the inventive concepts and are in no way to be taken as limiting to the invention as claimed.

DESCRIPTION OF THE PREFERRED EMBODIMENTS

Figure 1:
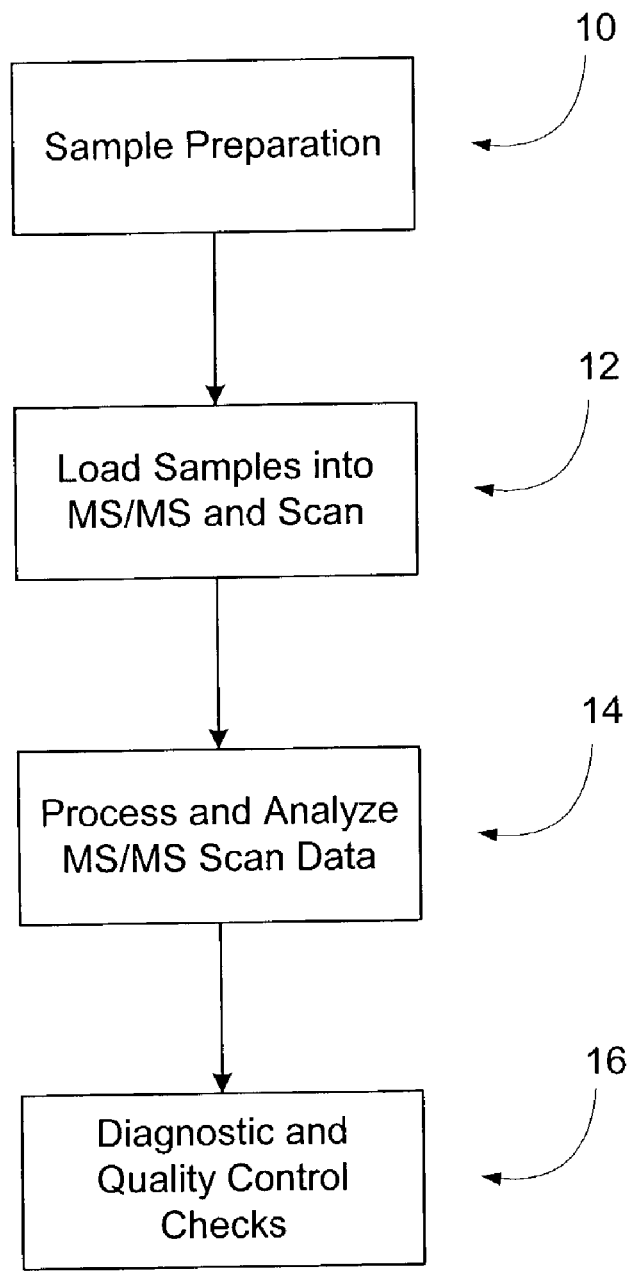
FIG. 1 is a simplified block diagram showing the overall method according to preferred embodiments of the present invention.

The methods will now be described in detail in relation to a preferred embodiment and implementation thereof that is exemplary in nature and descriptively specific as disclosed. As is customary, it will be understood that no limitation of the scope of the invention is thereby intended. The invention encompasses such alterations and further modifications in the illustrated implementations of the methods, and such further applications of the principles of the invention illustrated herein, as would normally occur to persons skilled in the art to which the invention relates.

The methods of the present invention involve plasma specimen collection from patients, with specimens then being spotted and dried on collection filter paper. The invention then utilizes appropriate preparation and analysis steps to produce quantitative data for comparison with similarly produced data for known calibration samples and quality control samples prepared from dialyzed plasma. Accurate quantification of the concentration of free carnitine, acylcarnitines, and total carnitine is then obtained by comparison to a calibration curve produced from data regarding the calibration curve samples.

According to embodiments of the present invention, plasma samples can be collected from a dialysis patient before, during, and/or after each dialysis session for subsequent spotting on filter paper to produce a dried patient sample. The filter paper used for holding and transporting dried plasma spot samples according to the present invention can be of any suitable type, including grade 903 filter paper made available from Schleicher and Schuell, and preferably is rectangular in shape and marked so as to be divided into four quadrants. In this manner, a single filter paper can be advantageously used according to the present invention to provide multiple samples from a single patient, including two or more identical plasma spots (so as to reduce chances of contamination or destruction) or up to four different samples taken at different times (such as before, during and after dialysis) from the same patient. Preferably, the filter paper also has one or more circles printed thereon to serve as targets for the plasma spots so as to assist the specimen collector at the dialysis location in spotting the plasma on the filter paper and to assist a lab technician in identifying and recovering the plasma for later analysis. The patients' plasma spot samples, once sufficiently dried as spots on the filter paper, can be sent in sealed envelopes (such as via overnight mail) to a remote laboratory location for analysis as such dried plasma samples have been found to remain stable at room temperature for up to one week.

According to the invention, such dried plasma samples taken from dialysis patients can be analyzed according to any suitable assaying method, including enzymatic assays, HPLC, and MS/MS. According to preferred embodiments of the present invention as hereinafter described in detail, however, analysis of the plasma samples is performed by electrospray MS/MS. This assaying technique is preferred in part because it allows for the simultaneous determination of free carnitine, acylcarnitines, and total carnitine concentrations in a single analytical run.

According to such preferred embodiments of the invention, once received at the laboratory, the dried plasma specimens are prepared by reconstitution with an internal standard-containing alcohol and then derivatized. Prepared samples are analyzed to quantify free carnitine, acylcarnitines and total carnitine concentrations (relative to that of the internal standards) in the patient samples, in known calibration curve samples and in known quality control samples where the calibration curve samples and quality control samples are prepared by the laboratory from dialyzed plasma. The results of the quantification assays of the various samples are then computed to quantify free carnitine, acylcarnitines and total carnitines in the dried patient samples while accounting for, among other things, various sample collection and preparation complications, hydrolysis of acylcarnitines, interference by glutamate, and mass-spectrometer performance.

In such embodiments of the present invention, dried calibration curve samples having various known compositions are prepared from dialyzed plasma and purified free L-carnitine inner salt. Five appropriate calibration curve samples comprising free L-carnitine spiked into dialyzed plasma from a methanol:water solution are itemized below in Table 1. As seen in the table, the calibration curve plasma samples have a known free carnitine concentration that corresponds to the particular free carnitine calibration curve stock solution used to prepare the plasma spot.

TABLE 1

| Free Carnitine in Plasma Calibration Curve Solution Used (FCxxxx) | Free Carnitine Concentration in Spotted Plasma Samples ($\mu$M) |
|---|---|
| FC4000 | 40 |
| FC2000 | 20 |
| FC1000 | 10 |
| FC0500 | 5 |
| FC0000 | 0 |

To prepare the calibration curve solutions ("FCxxxx") indicated above, the following procedure can be used. An appropriate amount of free L-carnitine inner salt is dissolved into a 50:50 HPLC-grade methanol-water solution to make a reconstituted free carnitine concentrated calibration curve 1 mg/mL solution. The concentration of this concentrated calibration curve solution should be 6.203 mM. Next, a first calibration curve stock solution, FC4000, is prepared by diluting 1074 µL of the concentrated calibration curve solution with 3926 µL of the 50:50 HPLC-grade methanol-water solution. The concentration of the free L-carnitine in solution FC4000 should be 1.333 nmol/µL. Calibration curve stock solution FC2000 is then prepared by diluting 2 mL of FC4000 with 2 mL of the 50:50 HPLC-grade methanol-water solution. Subsequent sequential 1:1 dilutions in 50:50 HPLC-grade methanol-water solution are then used to prepare calibration curve stock solutions FC1000 and FC0500. The 50:50 HPLC-grade methanol-water solution is used as calibration curve solution FC0000.

To prepare the calibration curve plasma samples as depicted above in Table 1, 1 mL of dialyzed plasma is combined with 30 µL of each calibration curve stock solution FCxxxx to produce the free carnitine concentrations indicated. To prepare the dried samples, 25 µL of these plasma solutions are then spotted onto the same type of filter paper used to collect the patient plasma samples and allowed to dry at room temperature (typically at least 2.5 hours). These dried calibration curve plasma samples have approximately the same stability as the patient plasma samples, and can be further preserved for later use (up to about 3 months) by storing the dried calibration curve samples at −20° C.

Additionally in such embodiments of the present invention, dried quality control samples having various known compositions are prepared from dialyzed plasma and purified free L-carnitine inner salt and acetylcarnitine hydrochloride. Like with the preparation of calibration curve plasma samples as described above, the preparation of quality control plasma samples according to embodiments of the present invention first comprises the preparation of several carnitine-containing quality control solutions for mixing with dialyzed plasma. In preferred embodiments, these quality control solutions, all having 50:50 HPLC-grade methanol-water solution as the solvent, include a free carnitine stock solution ("FC-S"), a free carnitine working solution ("FC-W"), an acetylcarnitine stock solution ("C2-S") and an acetlycarnitine working solution ("C2-W"). Solution FC-S is prepared to have a carnitine concentration of 2 nmol/µL, and solution FC-W is prepared therefrom via dilution to have a carnitine concentration of 0.5 nmol/µL. Likewise, solution C2-S is prepared to have a carnitine concentration of 4 nmol/µL, and solution C2-W is prepared therefrom via dilution to have a concentration of 1 nmol/µL.

Once the necessary quality control solutions are prepared, various quality control plasma solutions (QCyyyy) can be prepared by combining 5 mL of dialyzed plasma with combinations of the quality control solutions and a pure HPLC-grade methanol:water solution as indicated below in Table 2.

TABLE 2

| Plasma Sample (QCyyyy) | FC-S volume added (mL) | FC-W volume added (mL) | C2-S volume added (mL) | C2-W volume added (mL) | 50:50 MeOH:water volume added (mL) |
|---|---|---|---|---|---|
| QC0000 | 0 | 0 | 0 | 0 | 2 |
| QC0010 | 0 | 0 | 0 | 1 | 1 |
| QC0040 | 0 | 0 | 1 | 0 | 1 |
| QC0500 | 0 | 1 | 0 | 0 | 1 |
| QC0510 | 0 | 1 | 0 | 1 | 0 |

TABLE 2-continued

| Plasma Sample (QCyyyy) | FC-S volume added (mL) | FC-W volume added (mL) | C2-S volume added (mL) | C2-W volume added (mL) | 50:50 MeOH:water volume added (mL) |
|---|---|---|---|---|---|
| QC0540 | 0 | 1 | 1 | 0 | 0 |
| QC2000 | 1 | 0 | 0 | 0 | 1 |
| QC2010 | 1 | 0 | 0 | 1 | 0 |
| QC2040 | 1 | 0 | 1 | 0 | 0 |

By way of explanation, it can be determined from Table 2 above that quality control plasma solution QC0510 is prepared by mixing 1 mL of FC-W and 1 mL of C2-W into 5mL of dialyzed plasma, and quality control plasma solution QC0040 is likewise prepared by mixing 1 mL of C2-S and 1 mL of 50:50 HPLC-grade methanol:water into 5 mL of dialyzed plasma. Following the procedure indicated in Table 2, nine different quality control samples QCyyyy can be produced having the free carnitine concentrations ("[FC]") and acetylcarnitine concentrations ("[C2]") indicated below in Table 3.

TABLE 3

| Plasma (QCyyyy) | Plasma [FC] (µM) | Plasma [C2] (µM) |
|---|---|---|
| QC0000 | 0 | 0 |
| QC0010 | 0 | 10 |
| QC0040 | 0 | 40 |
| QC0500 | 5 | 0 |
| QC0510 | 5 | 10 |
| QC0540 | 5 | 40 |
| QC2000 | 20 | 0 |
| QC2010 | 20 | 10 |
| QC2040 | 20 | 40 |

As with the calibration curve plasma samples, dried quality control samples are prepared by spotting 25 µL of the quality control plasma solutions onto the same type of filter paper used to collect the patient plasma samples and allowed to dry (again, typically taking at least 2.5 hours at room temperature). These dried quality control plasma samples also have approximately the same stability as the patient plasma samples, and can be further preserved for later use (up to about 3 months) by storing at −20° C.

Referring now to FIG. 1, there is represented an overview of a method according to preferred embodiments of the present invention for quantifying carnitine concentration levels which can be utilized in diagnosing the extent of carnitine deficiency in dialysis patients within a clinical diagnostic setting. The method involves four main steps that collectively provide rapid, automated, and accurate sample analysis. Efficient sample preparation 10 of the dried plasma samples (patient plasma samples, calibration curve samples, and quality control samples are all prepared for analysis in like fashion) is necessary to insure accurate derivatization of the carnitine in the samples and constant and quantifiable hydrolysis of acetylcarnitines to free carnitine. Labeled internal standards are combined with the patient samples during their preparation to provide reference for quantification. After sample preparation 10, the samples are injected 12 into the electrospray tandem mass spectrometer. As is known in the art, an electrospray tandem mass spectrometer can be advantageously adapted to implement many automated sample-handling procedures to insure the speed and consistency of sample scanning. Data is then obtained from the MS/MS scans of the patient samples and calibration curve samples and subsequently processed to quantify carnitine levels in all of patient plasma samples in step 14. At this step, preferably values produced from the scan of the mass spectrometer are processed and printed into spreadsheet form to further allow checking of the calculations, a means of assuring accurate number production and quality. Furthermore, all spectra data is kept accurate using system diagnostic checks and quality control samples as seen in step 16. To assure diagnostic accuracy and sample quality, periodic system integrity checks and control samples that include specific additives are employed. In combination, the above-mentioned steps maximize the rate and quality at which plasma samples are analyzed for carnitine levels to result in a method that is suitable for use in the clinical setting.

Figure 2:
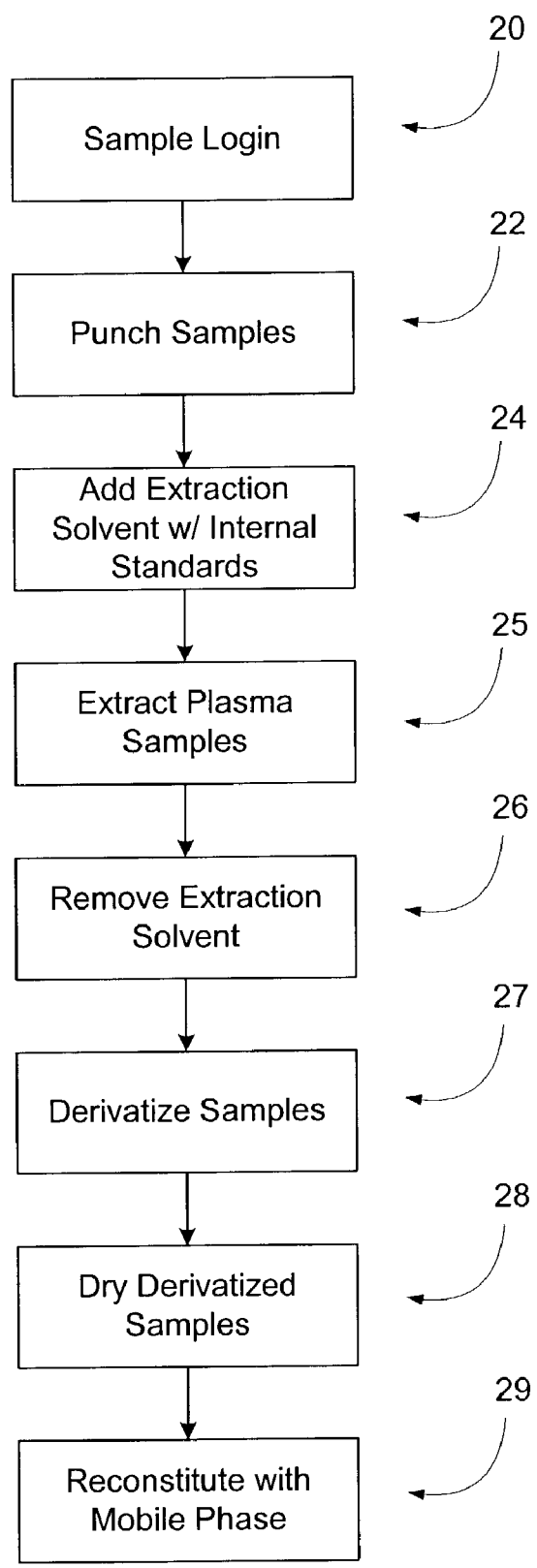
FIG. 2 is a block diagram showing in more detail the steps involved in preparing the sample.

FIG. 2 shows an overview of the sample preparation procedure (step 10 of FIG. 1) used in preferred embodiments of the present invention. An initial sample login 20 is performed by coding each sample, thereby associating the sample to a specific location of a microtiter well in a microtiter plate. The samples consist of plasma spots placed on designated areas of filter paper. After each spot is punched 22, such as into disks with an automated puncher (such disks typically having a diameter in the range of 3/16 in to 1/8 in, and preferably 3/16 in), it is placed into the designated microtiter well of a flat-bottom microtiter plate. Internal standard preparations, which were prepared with methanol or some other suitable alcohol that serves as an extraction solvent, are then added 24 to the dry punched plasma spot in each well. Such additions 24 are preferably performed using automated sample handling equipment.

The methanol, or other suitable alcohol employed, in the internal standards preparations serves as the solvent extraction solvent while the internal standards serve to quantify the free carnitine and acylcarnitines in the dried plasma matrix of each sample. In embodiments of the invention, the internal standard preparations are adapted to comprise an ideal mix of acylcarnitine/carnitine deuterium-labeled standards dissolved in an extraction solvent. As will be understood by one skilled in the art, the internal standards are provided in the extraction medium for the optimum mixed-mode scan functions to maximize carnitine detection. A list of the free carnitine and acylcarnitine internal standards used in preferred embodiments of the invention are listed below in Table 4. A suitable extraction solvent containing labeled internal standards can be prepared according to the following procedure. A set of isotopically labeled L-carnitine and L-acylcarnitine standards, such as in solid form, can be commercially obtained so as to facilitate the preparation of mixtures wherein the stoichiometric ratios of the carnitines are known. According to preferred embodiments of the present invention, the labeled L-carnitine and L-acylcarnitines include [$D_9$]carnitine, [$D_3$]acetylcarnitine, [$D_3$]propionylcarnitine, [$D_3$]butyrylcarnitine, [$D_9$]isovalerylcarnitine, [$D_3$]octanoylcarnitine, [$D_9$]myristoylcarnitine and [$D_3$]palmitoylcarnitine and are present in the internal standard in the molar ratio 20:5:1:1:1:1:1:2 as depicted in Table 4 below.

TABLE 4

| Labeled Internal L-Carnitine Standards | IS-Reconstituted (μmol/L) | IS-Stock (μmol/L) | IS-Working (μmol/L) |
|---|---|---|---|
| [$D_9$] carnitine | 152.00 | 19.00 | 0.127 |
| [$D_3$] acetylcarnitine | 38.00 | 4.75 | 0.031 |
| [$D_3$] propionylcarnitine | 7.60 | 0.95 | 0.006 |
| [$D_3$] butyrylcarnitine | 7.60 | 0.95 | 0.006 |
| [$D_9$] isovalerylcarnitine | 7.60 | 0.95 | 0.006 |
| [$D_3$] octanoylcarnitine | 7.60 | 0.95 | 0.006 |
| [$D_9$] myristoylcarnitine | 7.60 | 0.95 | 0.006 |
| [$D_3$] palmitoylcarnitine | 15.20 | 1.95 | 0.013 |

A suitable internal standard working solution for analyzing individual 3/16 in punched plasma spot disks, such as solution "IS-Working" in Table 4 above, can be prepared according to the following procedure. The various labeled L-carnitine and L-acylcarnitines are reconstituted in HPLC-grade methanol (or other suitable extraction solvent alcohol) to form a reconstituted internal standard solution having the solute standard concentrations of solution IS-Reconstituted in Table 4. A concentrated stock internal standard solution ("IS-Stock" in Table 4) is then prepared by diluting 500 μL of solution IS-Reconstituted in 3500 μL of an HPLC-grade 50:50 methanol:water solution to achieve a 1:8 dilution of the internal standards. Finally, a working extraction solvent solution ("IS-Working") containing the labeled internal standards for use in recovering the plasma from the dried samples is prepared by making a 1:150 dilution of solution IS-Stock in HPLC grade methanol. IS-Working is used in preparing the dried plasma samples for tandem mass spectrometry as will be described below.

The concentrations of the internal standards in IS-Working solution can, of course, be readily adjusted to analyze two 3/16 in or two 1/8 in dried plasma spots, a single 3/16 in or 1/8 in dried plasma spot, etc., by adjusting the volume of the extraction solvent additions to the analyzed samples or the concentration of the IS-stock solution in a manner as will be apparent to one skilled in the art. The working standard solution IS-Working thereby serves as both the extraction solvent and the means for internal standardization of the analysis.

In these preferred embodiments of the invention, each analytical run of the MS/MS includes a combination of calibration curve dried plasma samples and quality control dried plasma samples along with the patient specimen samples which one desires to have analyzed for carnitine concentrations. For example, all five different calibration curve plasma samples (FC4000, FC2000, FC1000, FC0500, FC0000) and any two randomly selected quality control samples (such as QC0000 and QC2040, or QC2010 and QC0040) can be interspersed with patient plasma samples on each microtiter plate introduced into the electrospray mass spectrometer for analysis. This procedure helps establish a calibration curve for analyzing the patient plasma samples and methods to account for various inconsistencies and errors produced in the MS/MS preparation and analysis. All three types of dried plasma samples are prepared for analysis according to the same procedure indicated in FIG. 2.

Referring again to FIG. 2, in preferred embodiments of the invention, dried calibration curve plasma samples, dried quality control plasma samples and dried patient plasma samples are first punched into recorded wells of a flat bottom microtiter plates, such as with a Wallac DBS puncher fitted with a 3/16 in punch head, at steps 20 and 22. Next, at step 24, an appropriate amount, such as 300 μL, of an internal standard-containing working solution (e.g., IS-Working) is added to each sample in the plate. This solvent addition can be advantageously automated by using a Gilson liquid handling system. The microtiter plate containing the mixture of all three types of samples is then agitated on rotator for approximately 30 minutes to extract plasma 25 from the dried plasma sample disks.

The extract from each sample is then transferred from the flat bottom microtiter plate to a round bottom plate, such as via the Gilson liquid handling system, to allow for further processing. The solvent from the internal standard is then removed 26 via evaporation, preferably under a gentle stream of nitrogen using a SPE-Dry nitrogen evaporator. In embodiments of the invention wherein samples are derivatized, each sample in the microtiter plate then undergo esterification 27. This is done by first adding an appropriate amount of acidified alcohol, such as via an Eppendorf pipette. Preferably, the derivatizing agent comprises 50 $\mu$L of 3 mol/L HCl in n-butanol to each sample well. In the esterification step, the samples in the microtiter plate are then covered with blue septa sheet fitted to the size of the plate, and then with a metal plate before the plate is placed in an oven and heated to stimulate derivatization. Preferably, the heating occurs at approximately 65° C. for about 15 minutes.

The derivatized specimens are then immediately dried 28 in the nitrogen evaporator as before to remove the volatile derivatization agent. After this drying step to remove derivatization agent, the samples are then reconstituted 29 by adding mobile phase, typically about 100 $\mu$L, by means of the Gilson liquid handler. The microtiter plate is then sealed with a clear micromat plate cover before analysis to retard evaporation of the mobile phase.

As described herein, preferred embodiments of the present invention employ derivatization of the carnitines in the plasma samples in order to increase sensitivity of the assay. optionally, of course, the derivatization step can be omitted from the assay when appropriate, such as when relatively larger carnitine concentrations are being quantified.

Before sample analysis, optimization of the MS/MS systems is achieved by regular injection of a tuning solution, such as daily. In preferred embodiments, the sensitivity threshold is determined from scans of [$D_5$]phenylalanine which should have a sensitivity of about at least 25% with a maximum intensity set to $5 \times 10^6$ counts per second ("cps"). The electrospray MS/MS system employed according to these preferred embodiments is a low flow rate system employing the use of a fused silica line displaced to the tip of the electrode. Automated injection systems use the fused silica line to directly connect the injector to electrode tip to minimize dead space. The mobile phase flow rate of the MS/MS can be set to about 18.0 $\mu$L/min and the injection volume can be set to about 15 $\mu$L to achieve reliable results with about a 2 minute cycle time. The scans implemented to detect the necessary fragments of the ions include positive SRM and positive precursor scans. Suitable instrument parameters, which may be adapted as is known in the art for optimization, are depicted below in Table 5.

TABLE 5

| MS/MS Instrument Parameters | Suggested Value |
|---|---|
| Nebulizing Gas ("Neb") | 9 |
| Curtain Gas ("Cur") | 7 |
| Ion Spray ("IS") (eV) | 5100 |
| Collision Gas ("CAD") | 3 |
| Declustering Potential ("DP") (eV) | 29 |
| Focusing Potential ("FP") (eV) | 120 |

TABLE 5-continued

| MS/MS Instrument Parameters | Suggested Value |
|---|---|
| Entrance Potential ("EP") (eV) | −10 |
| Collision Cell Exit Potential ("CXP") (eV) | 5 |

Furthermore, an example of suitable general scan parameters are provided below in Table 6.

TABLE 6

| Scan Parameter | Value |
|---|---|
| Peak Hopping | on |
| Step Size | 1.00 amu |
| Mass Defect | 100.00 mmu (per 100 amu) |

An example of suitable scan parameters specifically for the positive SRM scans are listed below in Table 7.

TABLE 7

| Q1 Mass (amu) | Q3 Mass (amu) | Time (msec.) | CE (eV) |
|---|---|---|---|
| 218.25 | 103.10 | 200.00 | 26.00 |
| 221.25 | 103.10 | 200.00 | 26.50 |
| 227.25 | 103.10 | 200.00 | 27.50 |

Similarly, an example of suitable scan parameters specifically for the positive precursor scans (for precursor of 85.05amu) are listed below in Table 8.

TABLE 8

| Start (amu) | Stop (amu) | Time (msec.) | CE Ramp (eV) |
|---|---|---|---|
| 258.00 | 486.00 | 445.00 | 29.00–59.00 |

After the MS/MS scans are preformed according to the present invention, the data obtained must be analyzed to calculate free carnitine, acylcarnitines, and total carnitine concentrations present in the patient samples. Preferably, these calculations are automated using a computer and appropriate MS/MS data acquisition and commercial data manipulation software. A suitable data acquisition software includes the Chemoview software and Analyst software programs made available from Applied Biosystems. Specifically, the Chemoview software enables automated calculation of the relative ratios of an analyte (e.g. free L-carnitine) to its internal standard (i.e., [$D_9$]L-carnitine) by allowing the user to define analyte masses of interest and associate relevant internal standard masses and desired internal standard concentration therewith. The data acquisition software also multiplies the analyte-to-standard mass ratio by the concentration of the internal standard to quantify the concentration of the analyte. Unfortunately, the hydrolization of acylcarnitines into free carnitine and the relative amounts of internal standard to analyte requires corrections to the analyte concentrations provided by the data acquisition software. Preferably, these corrections are thereafter performed by the data manipulation software (such as as, for example, a commercially available spreadsheet program).

First, a post-acquisition data correction must be made to adjust for the relative concentrations of the unknown analytes in the analyzed plasma samples by estimating the volume of plasma typically recovered from the punched disk (the amount and concentration of the internal standards being known). Assuming 25 μL of plasma were spotted on the filter paper, empirical observation concludes that a 25 μL spot on suitable filter paper produces a spot having an average diameter of 13.4 mm, or equivalently a radius (assuming a circular shape) of 6.7 mm (or 0.264 in). The average surface area of a 25 μL plasma spot on filter paper then would be about 0.219 in$^2$ (calculated using the standard equation for the area of a circle). One could also calculate that a 3/16 in diameter punch would produce a disk having a surface area of 0.0276 in$^2$ while a 1/8 in punch would produce a disk having a surface area of 0.0123 in$^2$. Thus, it is apparent that all of the plasma sample spotted on the filter paper will not be recovered by either a 1/8 in or 3/16 in punch. Therefore a smaller volume of plasma (and the carnitine it contains) than the full 25 μL will be reconstituted. To account for this factor, one can estimate the volume contained in a punch according to the following equation i whereby:

$$\text{Vol.} = 25 \, \mu L * (\text{Area}_{Punch}/\text{Area}_{Average\ Plasma\ Spot}) \quad \text{(equation i)}$$

Thus, where a 3/16 in punch is used, one can estimate that approximately 3.2 μL of plasma is contained in a disk punched from the dried plasma samples.

This average volume of plasma contained in a punched disk can then be used to obtain a conversion factor for each analyte to apply against the concentrations obtained from the data acquisition software. According to the procedure outlined above, for [D$_9$]L-carnitine about 300 μL of IS-W is added to each punched plasma disk, which means that approximately 38 pmol total of [D$_9$]L-carnitine is mixed with the 3.2 uL of plasma that is reconstituted from the 3/16 in disk. Thus, the concentration of [D$_9$]L-carnitine in the analyzed plasma for each sample is known to be approximately 11.9 μmol/L. Data acquisition softwares for use with tandem mass spectrometers typically provide either relative concentrations of each analyte with respect to their corresponding internal standards or alternatively provide baselined absolute concentrations of each analyte by assuming a baseline concentration for its internal standard. The conversion factor therefore allows the calculation of an accurate absolute concentration of each analyte. For example, since Chemoview assumes a nominal internal standard concentration of 10 mmol/L, the conversion factor to multiply the L-carnitine concentration data is 1.19 (11.9 μmol/L actual/ 10.00 μmol/L nominal). Similar calculations are applied to each analyte to obtain similar conversion factors and internal standard volume-adjusted data.

The data from the known calibration curve samples is used by the computer to interpolate the concentration values of carnitine in the patient and quality control samples by the construction of calibration curves. The calibration curves, or standard curves, produced by the data acquisition software allows for interpolated concentrations to be taken as the true concentrations in a manner as is known in the art.

This volume-adjusted raw data (comprising MS/MS volume adjusted concentrations of analytes) is then exported to a data manipulation software package, such as a spreadsheet program, to apply equations ii through v below to correct for glutamic acid interference and hydrolysis of acylcarnitines into free carnitine.

Analyses using MS/MS must account for the fact that mass spectrometers cannot readily distinguish analytes with the same molecular masses that also have the same product ions and molecular ions (such as isotopes). An example of such problematic analytes are leucine and isoleucine. However, it is known that if no product ions are shared, then ions of the same molecular mass do not interfere in MS/MS analyses. Although the butyl ester of glutamic acid and acetylcarnitine do not have the same molecular masses (259 m/z and 260 m/z, respectively), the protonated form of glutamic acid shares the same molecular ion mass of acetylcarnitine (260 m/z). Glutamate has physiological concentrations 10–100 times greater than acetylcarnitine. Therefore, the signal at 260 m/z, used for the detection of acetylcarnitine, is also affected by the glutamic acid contribution. However, the natural isotopic abundance of glutamic acid, and particularly its protonated form, could be used for estimating the contribution of glutamic acid to the signal for the detection of acetylcarnitine. According to embodiments of the invention, the contribution of glutamate at 260 is calculated by referencing the signal at 261 since 261 is also the M+1 natural isotopic abundance of acetylcarnitine (sometimes abbreviated herein as "C2"). A corrective formula is employed that first estimates the isotopic contribution at 261 by acetylcarnitine. The difference between the estimated contribution at 261 by acetylcarnitine and the actual raw data represents the contribution from glutamate. Finally, using the doublet of nearly equal intensity for glutamate at 260, the actual concentration of acetlycarnitine can be determined.

To get a corrected acetylcarnitine concentration that accounts for glutamic acid interference (i.e., "C2$_{Corrected}$"), equation ii below is employed, whereby:

$$C2_{Corrected} = C2_{Measured} - C2_{Glutamate} \quad \text{(equation ii)}$$

wherein C2$_{Measured}$ is the volume-adjusted actual acetylcarnitine concentration value provided by the data acquisition software, and C2$_{Glutamate}$ is the actual glutamate contribution. C2$_{Glutamate}$ can be determined from the following equation iii, whereby:

$$C2_{Glutamate} = \text{Glutamate}_{261} - C2_{Iso} \quad \text{(equation iii)}$$

wherein Glutamate$_{261}$ is the volume-adjusted actual glutamate concentration value at 261 provided by the data acquisition software, and C2$_{Iso}$ is the estimated isotope concentration at 261 of acetylcarnitine. C2$_{Iso}$ in turn can be estimated from the following equation iv, whereby:

$$C2_{Iso} = 0.14 \times C2_{Measured\ at\ 260} \quad \text{(equation iv)}$$

wherein the value of factor 0.14 is the determined M+1 natural abundance contribution of acetylcarnitine, and C2$_{Measured\ at\ 260}$ is the volume-adjusted actual acetlycarnitine concentration value at 260 provided by the data acquisition software.

To obtain corrected values of free carnitine concentration in a patient sample that accounts for acylcarnitine hydrolysis, equation v is employed, whereby:

$$FC_{Corrected} = FC_{Measured} - FC_{Hydrolyzed} \quad \text{(equation v)}$$

wherein FC$_{Measured}$ is the volume-adjusted actual free carnitine concentration value for a given sample as provided by the data acquisition software, and FC$_{Hydrolyzed}$ is the portion of FC$_{Measured}$ that is due to the hydrolysis of acylcarnitines into free carnitine. FC$_{Hydrolyzed}$ in turn can be calculated from the following equation vi, whereby:

$$FC_{Hydrolyzed} = \%_{Hydrolysis} \times AC \quad \text{(equation vi)}$$

wherein %$_{Hydrolysis}$ is the percent of measured free carnitine that is produced from hydrolysis of acylcarnitines, and AC is the volume-adjusted actual total acylcarnitine concentration value taking into account the corrected value for the concentration of acetylcarnitine. Given that the hydrolysis of acylcarnitines occurs at essentially a constant rate, the $\%_{Hydrolysis}$ can be calculated from the known internal standard concentrations by employing the following equation vii, whereby:

$$\%_{Hydrolysis} = [D_3]FC_{Hydrolyzed}/5.0 \ \mu M \quad \text{(equation vii)}$$

wherein $[D_3]FC_{Hydrolyzed}$ is the deuterated free carnitine concentration measured at 221 and the value 5.0 μM represents the concentration of deuterated acetylcarnitine internal standard utilized in the samples.

To calculate the actual total acylcarnitine concentrations ("AC"), equation viii is employed, whereby:

$$AC = \Sigma(C2_{Corrected}, C3, C4, C5:1, C5, C4OH, C6,\\ C5OH, C6OH, C8:1, C8, C8OH(C3DC), C10:2,\\ C10:1, C10, C4DC, C5DC(C10OH), C12:1,\\ C12, C6DC, C12OH, C14:2, C14:1, C14,\\ C14OH, C16:1, C16, C16OH, C18:2, C18:1,\\ C18) \quad \text{(equation viii)}$$

Finally, total carnitine concentration can be calculated from the corrected free and acylcarnitine concentrations according to equation ix below.

$$TC = FC_{Corrected} + AC \quad \text{(equation ix)}$$

The designations of the acylcarnitine butyl esters indicated above in equation viii can be recognized using the following Table 9 ("*" indicating an internal standard).

TABLE 9

| MS/MS Chemical Notation | Common Name | Butyl Ester ~m/z |
|---|---|---|
| C0 (Free) | L-Carnitine | 218 |
| d3-C0(Free) | L-Carnitine deuterated | 221 |
| d9-C0*(Free) | L-Carnitine deuterated i.s. | 227 |
| C2 | Acetyl | 260 |
| d3-C2* | Acetyl deuterated i.s | 263 |
| C3 | Propionyl | 274 |
| d3-C3* | Propionyl deuterated i.s. | 277 |
| C4 | Butyryl | 288 |
| d3-C4* | Butyryl deuterated i.s. | 291 |
| C4OH | 3-Hydroxy Butyryl | 304 |
| C5 | Isovaleryl | 302 |
| d9-C5* | Isovaleryl deuterated i.s. | 311 |
| C6 | Hexanoyl | 316 |
| C5OH | 3-Hydroxy Isovaleryl | 318 |
| C4DC | Methylmalonyl | 374 |
| C5:1 | Tiglyl | 300 |
| C6OH | 3-Hydroxy Hexanoyl | 332 |
| C5DC | Glutyryl | 388 |
| C8:1 | Octenoyl | 342 |
| C8 | Octanoyl | 344 |
| C6DC | Adipyl, Methyl Glutyryl | 402 |
| d3-C8* | Octanoyl deuterated i.s. | 347 |
| C8OH | 3-Hydroxy Octanoyl | 360 |
| C10:2 | Decadienoyl | 368 |
| C10:1 | Decenoyl | 370 |
| C10 | Decanoyl | 372 |
| C8DC | Suberyl | 430 |
| C10OH | 3-Hydroxy Decanoyl | 388 |
| C12:1 | Dodecenoyl | 398 |
| C12 | Dodecanoyl | 400 |
| C10DC | Dihydrosebacyl | 458 |
| C12OH | 3-Hydroxy Dodecanoyl | 416 |
| C14:2 | Tetradecadienoyl | 424 |
| C14:1 | Tetradecenoyl | 426 |
| C14 | Myristoyl | 428 |
| C12DC | dodecanoyldioic acid | 486 |
| d9-C14* | Myristoyl deuterated i.s. | 437 |
| C14OH | 3-Hydroxy Myristoyl | 444 |
| C16:1 | Palmitoleyl | 454 |

TABLE 9-continued

| MS/MS Chemical Notation | Common Name | Butyl Ester ~m/z |
|---|---|---|
| C16 | Palmitoyl | 456 |
| C14DC | tetradecanoydioic acid | 514 |
| d3-C16* | Palmitoyl deuterated i.s. | 459 |
| C16:1OH | 3-Hydroxy Palmitoleyl | 470 |
| C16OH | 3-Hydroxy Palmitoyl | 472 |
| C18:2 | Linoleyl | 480 |
| C18:1 | Oleyl | 482 |
| C18 | Stearoyl | 484 |
| C18:2OH | 3-Hydroxy Linoleyl | 496 |
| C18:1OH | 3-Hydroxy Oleyl | 498 |
| C18OH | 3-Hydroxy Stearoyl | 500 |

As will be appreciated by one skilled in the art, the above carnitine level quantification methods according to embodiments of the present invention can be advantageously utilized in diagnosing the extent of carnitine deficiency in dialysis patients within a clinical diagnostic setting. Such diagnosis could in turn be used by clinicians to select and implement appropriate preventative and treatment therapies including the intravenous administration of injectable levocarnitine following dialysis sessions for ESRD patients. It is possible that, in a clinical diagnostic setting, the above methods and constituent calculations may be interpreted so a proper course of action can be taken depending on the concentration levels of carnitine.

In order to facilitate the diagnosis of patients, decision trees could be used to interpret the level of the carnitine deficiency, and which is used to assist the user or interpreter in determining the next course of action and the significance of the concentration reading. While either the initial concentration values or the corrected values may be applied to the interpretation guide, it is, of course, preferred that the corrected values for acylcarnitine and free carnitine are used because of the heightened accuracy.

Various modifications of the embodiments herein disclosed will be readily apparent to one skilled in the art after reading the above. For example, any known suitable sample analysis assay can be used in alternative embodiments of the invention to determine the carnitine concentrations in the dried plasma samples. It will be understood that the above MS/MS methods and their concepts could be adapted to the analysis of other biological specimens, including urine, blood, spinal fluid, and tissue extracts (e.g., homogenized with an appropriate liquid vehicle and centrifuged). Any and all such modifications are intended to be covered by the application as claimed.

The invention claimed is:

1. A method for quantifying the carnitine concentration in a dialysis patient, comprising:
   obtaining one or more patient samples, said patient samples containing plasma collected from said patient;
   obtaining a plurality of calibration curve samples;
   preparing a plurality of patient samples and said calibration curve samples for analysis;
   analyzing said patient samples to produce patient data and said calibration curve samples to produce calibration curve data;
   comparing said patient data to said calibration curve data to obtain carnitine concentration data, said carnitine concentration data including a free carnitine concentration and an acetylcarnitine concentration for each patient sample; and, correcting said free carnitine concentration and said acetylcarnitine concentration to account for any errors introduced by hydrolysis or glutamic acid presence, said correcting also obtaining a quantified free carnitine concentration, a quantified total acylcarnitine concentration, and a quantified total carnitine concentration for each patient sample.

2. The method of claim 1, wherein said patient samples comprise drops of said plasma collected from said patient where said drops are dried on filter paper.

3. The method of claim 2, wherein said filter paper is segmented such that a single sheet can hold a plurality of dried samples from a given patient.

4. The method of claim 3, wherein said plurality of dried samples from a given patient are selected from the group consisting of pre-dialysis session plasma samples, post-dialysis session plasma samples, mid-dialysis session plasma samples, and combinations thereof.

5. The method of claim 2, wherein said plasma samples dried on filter paper are obtained via the mail for quantification.

6. The method of claim 2, wherein said filter paper containing dried drops of patient samples can be stored and transported at room temperature for approximately one week after being collected from said patient before being analyzed.

7. The method of claim 1, wherein said patient is an end stage renal disease patient that undergoes periodical dialysis sessions, and said patient samples comprise plasma collected from said patient before a dialysis session.

8. The method of claim 1, further comprising obtaining a plurality of quality control samples, and preparing and analyzing said quality control samples to produce quality control data.

9. The method of claim 8, wherein said analyzing of said samples is performed using tandem mass spectrometry, and said quality control data is utilized to fine tune equipment parameters for said tandem mass spectrometry.

10. The method of claim 2, wherein said quality control samples contain dialyzed plasma.

11. The method of claim 10, wherein said dialyzed plasma has mixed therein known concentrations of free carnitine and acetylcarnitine.

12. The method of claim 11, wherein said quality control samples comprise drops of said plasma dried on filter paper.

13. The method of claim 1, wherein said calibration curve samples contain dialyzed plasma.

14. The method of claim 13, wherein said dialyzed plasma has mixed therein known concentrations of free carnitine.

15. The method of claim 14, wherein said calibration curve samples comprise drops of said plasma dried on filter paper.

16. The method of claim 1, wherein preparing said plurality of plasma samples comprises extracting said plasma samples with an alcohol solution, said alcohol solution containing labeled internal standards.

17. The method of claim 16, wherein said labeled internal standards are selected from the group consisting of [D9]carnitine, [D3]acetylcarnitine, [D3]propionylcarnitine, [D3]butyrylcarnitine, [D3]isovalerylcarnitine, [D3]octanoylcarnitine, [D9]myristoylcarnitine and [D3]palmitoylcarnitine.

18. The method of claim 1, wherein said plasma samples comprise dried plasma spots on filter paper, said preparation of said plurality of plasma samples comprises punching a disk from said dried plasma spot for each plasma sample, and said quantified concentrations account for an estimated volume of said plasma spots recovered from said punched disks.

19. The method of claim 1, wherein said preparation of said plurality of samples comprises derivatizing recovered plasma samples with an acidified alcohol, and said correcting of said free carnitine concentration and said acetylcarnitine concentration accounts for any accompanying hydrolysis of acylcarnitines into free carnitine.

20. The method of claim 1, wherein said correcting of said free carnitine concentration and said acetylcarnitine concentration accounts for glutamic acid interference.

21. The method of claim 1, wherein said quantified concentration of said total acylcarnitine concentration is determined by summing a plurality of acylcarnitine butyl esters.

22. The method of claim 1, wherein said quantified total carnitine concentration is determined by summing said quantified total acylcarnitine concentration and said quantified free carnitine concentration.

23. The method of claim 1, further comprising tracking any changes in said quantified concentrations for a given patient over time by obtaining patient samples from a given patient wherein said samples originate from various dialysis sessions for said given patient.

24. A method for quantifying carnitine concentration levels in a patient undergoing dialysis procedures using tandem mass spectrometry, said method comprising:

taking patient plasma samples at each dialysis session, said plasma samples being spotted on filter paper and dried;

preparing said dried patient samples for tandem mass spectrometry;

analyzing said patient samples using tandem mass spectrometry to obtain an acetylcarnitine concentration, a total acylcarnitines concentration, and a free carnitine concentration;

correcting said acetylcarnitine concentration and total acylcarnitines concentration by accounting for interference from glutamic acid; and correcting said free carnitine concentration by accounting for hydrolysis of acylcarnitines.

25. The method of claim 24, wherein correcting said acetylcarnitine concentration comprises measuring a glutamate contribution, and subtracting said measured glutamate contribution from the acetylcarnitine concentration.

26. The method of claim 24, wherein correcting said free carnitine concentration comprises determining a percentage of hydrolysis of acylcarnitines, determining an amount of hydrolyzed acylcarnitines from said percentage, and subtracting said amount of hydrolyzed acylcarnitines from said free carnitine concentration.

27. The method of claim 24, wherein said corrected total carnitine concentration is calculated by adding said corrected total acylcarnitines concentration and said corrected free carnitine concentration.

28. The method of claim 24, wherein said patient samples are taken at a time selected from the group consisting of before a dialysis session, after a dialysis session, during a dialysis session, and combinations thereof.

29. The method of claim 24, further comprising sending said dried plasma samples through the mail to a remote location for analysis.

30. The method of claim 24, further comprising obtaining a plurality of quality control samples, and preparing and analyzing said quality control samples to produce quality control data.

31. The method of claim 30, wherein said quality control data is utilized to fine tune equipment parameters for said tandem mass spectrometry.

32. The method of claim 30, wherein said quality control samples comprise dried dialyzed plasma specimens having therein known concentrations of free carnitine and acetylcarnitine.

33. The method of claim 24, further comprising obtaining a plurality of calibration curve samples, and preparing and analyzing said calibration curve samples to produce a calibration curve for interpolating the concentrations of carnitine analytes.

34. The method of claim 33, wherein said calibration curve samples comprise dried dialyzed plasma specimens having therein known concentrations of free carnitine.

35. The method of claim 24, wherein preparing of said patient samples comprises extracting said plasma samples with an alcohol solution, said alcohol solution containing labeled internal standards.

36. The method of claim 24, wherein said preparation of said patient samples comprises derivatizing recovered plasma samples with an acidified alcohol, and said correcting of said free carnitine concentration and said acetylcarnitine concentration accounts for any accompanying hydrolysis of acylcarnitines into free carnitine.

37. The method of claim 24, further comprising tracking any changes in said corrected concentrations for a given patient over time by obtaining patient samples from a given patient wherein said samples are taken from various dialysis sessions for said given patient.

38. A method for assisting in the diagnosis of carnitine deficiency for a patient undergoing regular dialysis sessions, said method comprising:
 taking a patient plasma specimen for each dialysis session, each said specimen being dried on filter paper to create a patient sample;
 preparing a plurality of plasma samples, wherein said plasma samples include patient samples and calibration curve samples;
 analyzing said plasma samples using tandem mass spectrometry to produce patient data and calibration curve data;
 determining a free carnitine concentration and a total acylcarnitine concentration for said patient sample by comparison of said patient data to said calibration curve data; said determining of said free carnitine concentration comprising accounting for the hydrolysis of acylcarnitines into free carnitine; and
 applying at least one of said determined concentrations to facilitate diagnosing of said patient by comparing said at least one of said determined concentrations to one or more thresholds for one or more of said concentrations; said one or more thresholds representing a diagnosis of carnitine deficiency.

39. The method of claim 38, wherein determining of said acylcarnitine concentration comprises accounting for the interference of glutamic acid in the analysis of acetylcarnitine.

40. The method of claim 38, further comprising obtaining a plurality of quality control samples, and preparing and analyzing said quality control samples to produce quality control data.

41. The method of claim 40, wherein said quality control data is utilized to fine tune equipment parameters for a tandem mass spectrometer.

42. The method of claim 40, wherein said quality control samples comprise dried dialyzed plasma specimens having therein known concentrations of free carnitine and acetylcarnitine.

43. The method of claim 38, wherein said calibration curve samples are analyzed to produce a calibration curve for interpolating the concentrations of carnitine analytes.

44. The method of claim 38, wherein said calibration curve samples comprise dried dialyzed plasma specimens having therein known concentrations of free carnitine.

45. The method of claim 38, wherein preparing of said patient samples comprises extracting said plasma samples with an alcohol solution, said alcohol solution containing labeled internal standards.

46. The method of claim 38, wherein said preparation of said samples comprises derivatizing recovered plasma samples with an acidified alcohol.

* * * * *